US00RE33997E

United States Patent [19]

Kuzma et al.

[11] E Patent Number: Re. 33,997

[45] Reissued Date of Patent: * Jul. 14, 1992

[54] BIOLOGICALLY STABILIZED COMPOSITIONS COMPRISING COLLAGEN AS THE MINOR COMPONENT WITH ETHYLENICALLY UNSATURATED COMPOUNDS USED AS CONTACT LENSES

[75] Inventors: Petr Kuzma, Monmouth Junction; Giovanina Odorisio, Edgewater, both of N.J.

[73] Assignee: Allergan, Inc., Irvine, Calif.

[ * ] Notice: The portion of the term of this patent subsequent to Jun. 14, 2000 has been disclaimed.

[21] Appl. No.: 323,361

[22] Filed: Mar. 13, 1989

Related U.S. Patent Documents

Reissue of:

[64] Patent No.: 4,452,925
Issued: Jun. 5, 1984
Appl. No.: 232,749
Filed: Feb. 9, 1981

[51] Int. Cl.[5] ..... G02C 7/04

[52] U.S. Cl. ..... 523/106; 523/108; 527/201; 351/160 H

[58] Field of Search ..... 523/106; 351/160 H; 527/201

[56] References Cited

U.S. PATENT DOCUMENTS

| | | | |
|---|---|---|---|
| 4,035,330 | 7/1977 | Schultz | 260/29.6 R |
| 4,223,984 | 9/1980 | Miyata et al. | 351/160 H |
| 4,252,421 | 2/1981 | Foley, Jr. | 351/162 |
| 4,260,228 | 4/1981 | Miyata | 351/160 H |
| 4,264,155 | 4/1981 | Miyata | 351/160 H |
| 4,264,493 | 4/1981 | Battista | 260/117 |
| 4,268,131 | 5/1981 | Miyata et al. | 351/160 H |

*Primary Examiner*—Theodore Morris

[57] ABSTRACT

Hydrogels are prepared by subjecting to poymerization conditions an aqueous admixture comprising a major amount of an organic monomer which is characterized by a polymerizable ethylenic group as illustrated by N,N-dimethylacrylamide, 2-hydroxyethyl methacrylate, dimethylaminoethyl methacrylate or methoxytriethylene glycol methacrylate, and a minor amount of solubilized collagen. The reactants employed are at least partially soluble in the aqueous reaction medium. The hydrogels thus prepared are novel shaped articles having utility in the medical and cosmetic fields. Contact lenses of such hydrogels exhibit high water content, high oxygen permeability and good mechanical strength characteristics.

28 Claims, 4 Drawing Sheets

BIOLOGICALLY STABILIZED COMPOSITIONS COMPRISING COLLAGEN AS THE MINOR COMPONENT WITH ETHYLENICALLY UNSATURATED COMPOUNDS USED AS CONTACT LENSES

Matter enclosed in heavy brackets [ ] appears in the original patent but forms no part of this reissue specification; matter printed in italics indicates the additions made by reissue.

BACKGROUND OF THE INVENTION

This invention relates to the preparation of high water content synthetic hydrogels modified with minor amounts of natural polymers and to processes for producing the same. In one aspect, the invention relates to shaped articles fabricated from such hydrogels which are useful for medical and cosmetic purposes, e.g., soft contact lenses, therapeutic eye bandages, etc.

Hydrogels, i.e., gels which contain water, are well known in the art. They can be formed of various natural substances such as gelatin and the polysaccharides as well as various synthetic polymers such as crosslinked acrylamide polymers, polyelectrolyte complexes, and polymers of hydroxyalkyl acrylic esters. The outstanding biocompatibility characteristic of synthetic hydrogels of acrylic polymers or of unsaturated amide polymers, with living tissue, have made them particularly useful in alloplastic and prosthetic applications. Moreover, properties such as transparency, good optics, shape stability, inertness to chemicals and bacteria, etc., have made such hydrogels of acrylic polymers the material of choice in the production of daily wear soft contact lenses.

Synthetic hydrogels can be prepared having a wide variation in certain properties such as water uptake, mechanical properties, gas permeability, optical characteristics, etc. In various applications involving hydrogels certain properties are desired which are actually in conflict with each other. For example, extended-wear soft contact lenses, i.e., lenses which can be worn for days without removal from the eye as opposed to conventional or daily wear contact lenses which are removed from the eye on a daily basis, desirably should be characterized by high water uptake to achieve good diffusion properties and simultaneously, by good mechanical strength. However, it is recognized in the art that to attain hydrogels of very high water content, e.g., upwards of 90 weight percent, and more, other properties are usually sacrificed, e.g., such hydrogels exhibit relatively low mechanical properties.

U.S. Pat. No. 3,926,869 discloses the hardening of gelatin for use in photographic emulsion layers by incorporating into the gelatin an acrylic acid-acrylamide copolymer. The layers produced are said to be highly water-swellable.

U.S. Pat. No. 4,060,081 discloses a multilayer membrane useful as a synthetic skin, having a first layer which is a cross-linked composite of collagen and a mucopolysaccharide, to which is adhered a flexible film of polyacrylate or polymethacrylate ester or their copolymers which is flexible and which protects the cross-linked collagen layer from moisture. The collagen-mucopolysaccharide layer is typically produced by dispersing small amounts of collagen, for example, 0.3% by weight, in a dilute acetic acid solution and agitating the solution as the polysaccharide is slowly added dropwise into the collagen dispersion. The collagen and mucopolysaccharide coprecipitate into a tangled mass of collagen fibrils coated with mucopolysaccharide.

U.S. Pat. No. 4,161,948 discloses synthetic membranes for closing wounds, wherein it is disclosed that it is preferable that the α-amino acid polymers employed be cross-linked with a diol, such as polyoxyethylene glycol, in order to have properties resembling those of natural human collagen.

SUMMARY OF THE INVENTION

It has now been unexpectedly discovered that novel shape retaining hydrogels of high water content of upwards to about 95 weight percent water, based on the weight of the hydrogel, possessing good mechanical properties can be prepared by the practice of the invention described herein. Such hydrogels have been observed to possess additional desirable characteristics which make them highly useful in the cosmetic and medical areas. These novel hydrogels exhibit high transparency, good diffusion, good oxygen permeability, high optics, inertness to bacteria, chemicals, biocompatibility with living tissue, and other desirable properties.

The present invention also provides a novel process which comprises reacting an aqueous mixture comprising an ethylenically unsaturated compound and collagen both defined hereinafter under polymerization and/or crosslinking conditions for a period of time sufficient to produce the aforesaid novel shape-retaining hydrogels.

The present invention further provides a novel process for the preparation of novel hydrophilic plastic soft contact lenses, particularly those which can be worn on the eye for extended periods of time, e.g., upwards to several weeks if so desired, and to the novel contact lenses per se.

These and other objectives can be achieved by practicing the teachings herein disclosed and suggested to the art.

DESCRIPTION OF THE INVENTION

It was unexpectedly found that in the practice of various embodiments of the invention there could be produced novel hydrogels of high water content oftentimes having mechanical strength characteristics, e.g., tear strength, which were superior to relatively low water-containing hydrogels of sparingly crosslinked 2-hydroxyethyl methacrylate polymers, e.g., Hydron ® polymers. These characteristics together with properties described previously make the novel shape retaining hydrogels highly useful in the form of extended wear hydrophilic plastic soft contact lenses.

The novel hydrogels can be formed by various techniques known in the polymerization art. In general, there is formed a liquid mixture, desirably an aqueous dispersion or solution, comprising at least one ethylenically unsaturated compound, collagen, and optionally, a modifier.

The ethylenically unsaturated compound is characterized by a polymerizable carbon-to-carbon double bond, i.e.,

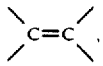

and is composed of (i) carbon, hydrogen, oxygen and nitrogen in the form of

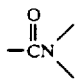

and optionally oxygen in the form of carbonyl

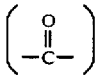

as exemplified by N,N-dimethylacrylamide and N-(1,1-dimethyl-3-oxobutyl)acrylamide, (ii) carbon, hydrogen, and oxygen in the form of carbonyloxy

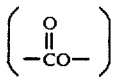

and hydroxyl (—OH), and optionally oxygen in the form of etheric oxygen (—O—), e.g., 2-hydroxyethyl methacrylate and diethylene glycol monomethacrylate, (iii) carbon, hydrogen, carbonyloxy oxygen and etheric oxygen, e.g., methoxytriethylene glycol methacrylate, (iv) carbon, hydrogen, carbonyloxy oxygen, and oxygen in the form of vicinal-epoxy, i.e.,

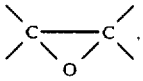

e.g., glycidyl methacrylate, or (v) carbon, hydrogen, carbonyloxy oxygen, and amino nitrogen,

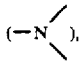

e.g., dimethylaminoethyl methacrylate.

The ethylenically unsaturated compound(s) which can be employed in the preparation of the novel hydrogels are at least partially miscible or otherwise compatible with water or with an aqueous solution of water-natural polymer or of water-($C_1$–$C_4$)alkanol as illustrated by the unsubstituted, N-substituted and N,N-disubstituted 2-alkenamides wherein each N substituent is hydrogen or a monovalent hydrocarbon radical such as aliphatic, cycloaliphatic, or aryl, desirably each N substituent is hydrogen or a monovalent saturated aliphatic hydrocarbon which preferably is a ($C_1$–$C_6$)alkyl and preferably still a ($C_1$–$C_4$)alkyl, e.g., methyl, ethyl, n-propyl, isopropyl, n-butyl, and n-hexyl, and wherein the 2-alkenoyl group of the 2-alkenamide molecule contains from 2–6 carbon atoms; the ethylenically unsaturated lactams, e.g., N-vinylpyrrolidone, N-vinylcaprolactam, and methyl-2-vinylpyrrolidone; the vicinal-epoxyalkyl 2-alkenoates wherein the vicinal-epoxyalkyl group desirably contains from 2 to 4 carbon atoms and wherein the 2-alkenoate group contains from 2–6 carbon atoms, e.g., glycidyl acrylate, glycidyl methacrylate, 2,3-epoxylbutyl methacrylate, and glycidyl crotonate; the esters of aliphatic polyhydroxy alcohols and ethylenically unsaturated monocarboxylic acids such as the hydroxy(alkoxy)$_n$alkyl 2-alkenoates wherein n is an integer having a value of zero and upwards to 4, wherein the alkyl and alkoxy substituents have from 2–4 carbon atoms, and wherein the 2-alkenoate group contains from 2–6 carbon atoms, e.g., 2-hydroxyethyl methacrylate, 2-hydroxyethyl acrylate, 2-hydroxypropyl acrylate, 2-hydroxypropyl methacrylate, 2-hydroxyethoxyethyl methacrylate, 2-hydroxyethoxyethyl acrylate, 2-hydroxypropoxyethyl methacrylate, and 2-hydroxyethyl crotonate; the alkoxy(alkoxy)$_n$alkyl 2-alkenoates wherein n, alkyl, alkoxy, and the 2-alkenoate group have the values assigned above, with the proviso that the terminal alkoxy substituent of the molecule contains from 1 to 4 carbon atoms, e.g., 2-methoxyethyl acrylate, methoxyethyl methacrylate, methoxydiethylene glycol methacrylate, methoxydiethylene glycol acrylate, methoxytriethylene glycol methacrylate, and methoxytriethylene glycol crotonate; the dialkylaminoalkyl 2-alkenoates wherein the alkyl substituents, individually, desirably contain from 1–4 carbon atoms and wherein the 2-alkenoate group contains from 2–6 carbon atoms, e.g., diethylaminoethyl methacrylate and dipropylaminoethyl methacrylate.

The ethylenically unsaturated amides which are particularly suitable in the preparation of the novel hydrogels can be represented by the following formula:

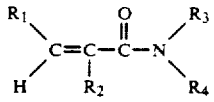

wherein $R_1$, $R_2$, $R_3$, and $R_4$, individually, can be hydrogen or lower alkyl, e.g., methyl, ethyl, propyl, butyl and the like, preferably $R_1$ and $R_2$ are hydrogen or methyl, and $R_3$ and $R_4$ are methyl or ethyl, preferably still $R_1$ is hydrogen, $R_2$ is methyl, and $R_3$ and $R_4$ are methyl or ethyl. Illustrative ethylenically unsaturated amides include acrylamide, methacrylamide, crotonamide, N-methylacrylamide, N,N-dimethylacrylamide, N-ethylacrylamide, N,N-diethylacrylamide, N-methyl-N-propylacrylamide, N-isobutylacrylamide, N-methylmethacrylamide, N,N-dimethylmethacrylamide, N-ethylmethacrylamide, N-methyl-N-butylmethacrylamide, N-cyclohexylmethacrylamide, N,N-dimethylcrotonamide, and N,N-diethylcrotonamide. Other illustrative amide compounds include diacetoneacrylamide, cinnamide, and the like.

As stated in U.S. Pat. No. 4,223,984, issued Sept. 23, 1980, collagen is a major protein of connective tissue such as skin, cornea, etc., and can be solubilized, separated and purified by the treatment with proteolytic enzymes (other than collagenase), e.g., proctase, pepsin, trypsin and pronase. Enzyme solubilized collagen is telopeptides-poor, relatively inexpensive, and useful as a biomedical material. The collagen can be redispersed as a clear aqueous gel, e.g., up to 30 weight percent but generally less due to the high viscosity, the balance being water or aqueous solution of water and a miscible inert, organic liquid, e.g., lower alkanol. A useful discussion of collagen appears in the article by K. Stenzel et al entitled "Collagen as a Biomaterial", Annual Review of Biophysics and BioEngineering 3: 231-53 (1974) and to the extent necessary to further describe the solubilized or chemically modified collagens which are contemplated in the practice of the invention(s) said article is hereby incorporated by reference into this disclosure as if it were set out in full text.

Solubilized collagen is defatted to the extent necessary whenever transparent collagen is required for the contemplated end use application, e.g., in the preparation of extended wear contact lenses. Solubilized collagen contains many $NH_2$ and COOH groups in its structure, and chemical modifications of the molecule can be readily made, e.g., all or some of the amino groups may be acylated by reaction with a mixture of acetic anhydride and acetic acid, or other anhydride such as succinic anhydride. All or some of the carboxyl groups contained in the molecule may be esterified by the standard reaction with acidified alcohol, preferably a water soluble aliphatic alcohol, such as methanol, ethanol, etc. In the above reactions the isoelectric point of collagen can be controlled, either negative or positive, or completely neutralized.

Crosslinking the solubilized collagen as well as crosslinking the ethylenically urfsaturated monomer(s) with-/without additional ethylenically unsaturated modifiers described hereinafter can be accomplished by various means. Crosslinking the solubilized collagen is described in the literature and can be accomplished by treating with various chemicals such as aldehyde, e.g., formaldehyde, acrolein, glutaraldehyde glyoxal, or with acids, e.g., chromic acid, or by irradiation, e.g., gamma-irradiation, ultraviolet light, etc. In the practice of highly desirable embodiments of the invention, the crosslinking of the solubilized collagen is effected under a nitrogen atmosphere in the shape-forming mold such as a lens mold using radiation dosages known in the art; see for example U.S. Pat. No. 4,223,984 issued Sept. 23, 1980.

Crosslinking the ethylenically unsaturated compound(s) with or without ethylenically unsaturated modifiers contained in the reaction mixture is most suitably effected through the use of crosslinking agents including, for instance, ethylene glycol diacrylate, ethylene glycol dimethacrylate, 1,2-butylene dimethacrylate, 1,3-butylene dimethacrylate, 1,4-butylene dimethacrylate, propylene glycol diacrylate, propylene glycol dimethacrylate, diethylene glycol dimethacrylate, dipropylene glycol dimethacrylate, diethylene glycol diacrylate, diethylene glycol crotonate, allyl maleate, triallyl melamine, N,N'-methylenebisacrylamide, glycerine trimthacrylate, divinyl ether, diallyl itaconate, ethylene glycol diester of itaconic acid, polyallyl glucose, e.g., triallyl glucose, polyallyl sucrose, e.g., pentaallyl sucrose, sucrose diacrylate, glucose dimethylacrylate, pentaerythritol tetraacrylate, sorbitol dimethacrylate diallyl aconitate, divinyl citraconate, diallyl fumarate, glycidyl acrylate, glycidyl methacrylate, allyl methacrylate, allyl acrylate, vinyl methacrylate. The cross-linking agents usually, but not necessarily, have at least two ethylenically unsaturated double bonds. Crosslinking of the ethylenic compound(s) can also be effected by means of irradiation.

Though not wishing to be held to any theory of reaction mechanism or theory, it appears that various reactions take place, desirably simultaneously, during the preparation of the novel hydrogels from the liquid medium comprising the reactants. Crosslinking of the solubilized collagen occurs as well as vinyl polymerization of the ethylenically unsaturated monomer(s) including the polyethylenically unsaturated crosslinker, if present in the liquid medium, and graft polymerization of the said monomer(s) and the said collagen. The novel hydrogels are characterized, from an inspection of their IR spectrum, as graft polymer/collagen products (ethylenically unsaturated monomer grafted to the collagen). Also, in view of the basic triple-helical structure of collagen and the polymerization between the ethylenic monomer(s) as well as between the monomer(s) and collagen, there is probably formed a network of interpenetrating polymer/collagen hydrogels.

The preparation of the novel hydrogels is preferably effected in an aqueous medium or a medium comprising water and alcohol which is miscible and compatible with water, e.g., methanol, ethanol, isopropanol, etc., and in which the reactants form a clear solution or gel desirably under an inert gas such as nitrogen, argon, etc. In the practice of the process invention it is desirable to form an aqueous solution or gel of the collagen. Such solutions or gels will generally contain less than 30 weight percent collagen in view of the highly viscous nature of the resulting aqueous medium comprising the collagen (and other reactant). Thus an aqueous solution comprising upwards to about 15 weight percent collagen is suitable. A solution or dispersion or gel which contains from about 0.5 to about 12 weight percent, based on the total weight of the liquid reaction mixture, is most desirable, from about 1 to about 10 weight percent collagen is preferred.

The reaction conditions will vary depending, to a significant degree, on the reactants of choice, catalyst, crosslinker, etc. In general, conventional types of polymerization known in the art can be employed, such as polymerization by high energy radiation, e.g., gamma or ultraviolet; solution polymerization in which the mixture comprises collagen, ethylenic monomer(s), a chemical crosslinking agent for collagen and monomer, and a redox initiation system for the monomer(s) such as sodium thiosulfate-potassium persulfate; etc. Each specific type of polymerization generally requires a specific set of conditions. For example, when gamma-radiation is used, the polymerization desirably is carried out at low temperature (under 30° C. and preferably below about 15° C.) and under an inert atmosphere in order to minimize degradation of the natural polymer component (collagen) due to high energy radiation. The resulting product is usually leached and equilibrated in an aqueous medium to remove traces of unreacted residual monomer(s), catalyst residues, etc.

The novel process is generally conducted with an amount of solubilized collagen that is less than 50 weight percent, generally not exceeding about 35 weight percent, of the total charge of reactants, i.e., collagen, ethylenic monomer, crosslinker and modifier, if present. The amount of ethylenically unsaturated monomer is at least about 50 and upward to 99.5 weight percent, and generally at least about 68 to about 90 weight percent. The use of collagen as low as one weight percent and lower, e.g., as low as 0.5 weight percent gives novel hydrogels of enhanced water uptake. Oftentimes the novel hydrogels exhibit enhanced mechanical properties as compared with the hydrogel prepared from a corresponding reaction mixture which lacks the collagen component therein. It is of interest to note that solubilized collagen is biodegradable material which characteristic limits its use as a material for extended wear hydrophilic plastic soft contact lenses; yet the novel hydrogels obtained by the practice of the novel process are non-biodegradable under the test conditions employed in the working Examples.

If desired, a modifier(s), i.e., compound(s) which possesses a polymerizable ethylenic carbon-to-carbon bond, can be incorporated into the reaction medium and caused to polymerize through its ethylenic bond and with the polymerizable ethylenic bond of the other reactant(s). By the practice of this embodiment there can be prepared novel hydrogels whose properties can be further altered and varied over a wide spectrum. There can be included in the reaction medium upwards to about 35 weight percent of modifier, based on the total weight of reactants. In general, the modifier, if employed, may comprise from about 1 to about 30, and desirably from about 3 to about 20 weight percent, based on the total weight of the reactants. It is apparent that the use of a modifier can appreciably alter the ultimate properties of the hydrogel to yield "tailor-made" products. Examples of modifiers include, by way of illustrations, the alkyl 2-alkenoates, e.g., methyl methacrylate, ethyl methacrylate, propyl methacrylate, butyl methacrylate, ethyl crotonate, butyl cinnamate, and the like; the 2-alkenoic acids, e.g., methacrylic acid, acrylic acid, and the like.

The reactants, i.e., collagen, ethylenic compound, and crosslinker and modifier, if employed, are miscible or soluble or partially soluble in water (at least to the extent necessary to prepare the novel hydrogels described herein) or soluble in a compatible water-organic liquid medium such as water-lower alkanol mixture. As indicated previously, the reaction medium can include, and desirably does include, a crosslinking agent(s). As indicated previously, crosslinking of the solubilized collagen and the ethylenic reactant can be accomplished by irradiation; also, either the collagen or the ethylenic reactant(s) can be crosslinked by irradiation and the other by chemical crosslinking agents; or both the collagen and ethylenic reactants can be crosslinked by chemical agents. The amount of crosslinking agent employed in the novel process will depend, to a significant degree, on the type of polymerization, the reactants of choice, the concentration of the reactants, the degree of water-uptake desired in the novel hydrogel, and other factors. For example, particularly suitable hydrogels of combined collagen/amide products can be obtained using a reaction medium which contains up to about 5 weight percent crosslinking agent, based on the total weight of reactants. More or less than 5 weight percent chemical crosslinker is within the scope of the invention. For the preparation of hydrogels of high water content, an amount not exceeding about 2 weight percent crosslinking agent is generally preferred.

The proportions of the combined components in the novel hydrogels are as follows:

| COMPONENT | BROAD(1) | PRE-FERRED(1) | MOST PRE-FERRED(1) |
|---|---|---|---|
| Ethylenic Compound | ~50–99.5 | ~60–95 | ~68–90 |
| Collagen | <50–0.5 | ~5–45 | ~10–35 |
| Modifier | 0–35 | 0–30(2) | 0–20(2) |

-continued

| COMPONENT | BROAD(1) | PRE-FERRED(1) | MOST PRE-FERRED(1) |
|---|---|---|---|
| Crosslinking Agent | 0–5 | 0–2 | 0–1 |

(1)Weight percent, based on total weight of combined components (excluded 60 water).

(2)A minimum of 1 to 3 weight percent modifier can alter the properties of the ultimate novel hydrogel.

The hydrogels obtained by the practice of the invention can possess a water content as high as 95 weight percent, based on the weight of the hydrogel. In general, shape-retaining novel hydrogels which are characterized by biocompatibility with living tissue, non-biodegradability under our test conditions, high oxygen permeability, transparency, water and various common chemicals, good optical geometry, and good mechanical properties. The novel hydrogels in the shape of contact lenses and which have a water content of at least about 55 weight percent, desirably at least about 65 weight percent, and preferably at least about 75 weight percent, are especially suitable as extended wear contact lenses. The upper limit with respect to the water content can be, as indicated previously, as high as 95 weight percent, generally upwards to about 90 weight percent.

The following Examples are illustrative and are not to be construed as limiting the invention(s). Certain materials employed in these Examples as well as methods of evaluation of certain characteristics of the resulting hydrogel product are described below.

Water content of the hydrogel is expressed as follows:

$$\text{Weight Percent } H_2O = \frac{\text{Hydrated Weight} - \text{Dried Weight} \times 100\%}{\text{Hydrated Weight}}$$

Mechanical strength is expressed as a "tear strength" which is a method employed in evaluation of soft contact lenses. The hydrogel test sample (about 10 mm in length and about 5 mm in width) is split initially at its width. The split end is fastened to an instrument equipped with a transducer and a recorder. The sample is kept in water during this test. The pulling force needed to tear the sample along its whole length (at the split) is recorded (in grams) and normalized for 1 mm thickness. All comparisons are based on Hydron® soft contact lens material having a water content of about 38 weight percent. The Hydron® material is prepared from a polymerizable mixture comprising about 99 weight percent hydroxyethyl methacrylate, about 0.3 to about 0.5 weight percent of ethylene glycol dimethacrylate, and diisopropyl peroxydicarbonate catalyst. Hydron® is a registered trademark of National Patent Development Corporation.

Oxygen permeability method used is the standard procedure used to measure the oxygen permeability of hydrogels (Y. Yasuda and W. Stone, J. of Polymer Sci., 4, 1314–1316 (1966)). A similar procedure can be used to measure the permeability of films (ASTM-Volume 27, D1344). Oxygen permeability of a hydrogel is primarily a function of the water content of the hydrogel. It can be either measured experimentally or interpolated from a graph constructed from values of oxygen permeability measured on hydrogel membranes of varying water content. The correlation of oxygen permeability values with hydrogels of 38, 58, 70 and 85 weight percent water content is shown in the Table I below:

TABLE I

| Weight % Water | Oxygen Permeability × $10^{-10}$(1) |
|---|---|
| 38 (Hydron ®) | 10.0 |
| 58 (Duragel ®) | 23.3 |
| 70 (Duragel ®)(2) | 34.8 |
| 85 (Permalens ®)(3) | 42.8 |

(1) $\frac{cm^3 \cdot cm}{cm^2 \cdot Hg\ sec}$
(at standard pressure, 34° C.) using Delta Scientific Model 2110, Dissolved Oxygen BOD and Temperature Analyzer.
(2)Duragel is a trademark of Cooper Laboratories, Inc.
(3)Permalens is a registered trademark of Cooper Laboratories, Inc.

Biological Stability: A soft contact lens material must be biologically stable, i.e., non-biodegradable. To determine the degree of resistance a material may exhibit to various strains of Pseudomonas aeruginosa, the following experiment is performed on each formulation of hydrogel material. Discs of the material measuring 14 mm in diameter and 0.5 mm in center thickness are immersed in 10 ml aliquots of nutrient media which have been inoculated with approximately $10^5$ viable cells per ml. Tubes are incubated at 37° C. and samples are inspected macroscopically each day for changes that may have appeared in edge and surface quality, clarity and mechanical strength. The experiment is concluded for each sample as soon as any change is observed. If no change is observed after 12 days the sample is considered non-biodegradable.

Boil 'N Soak ® is a registered trademark of Burton, Parsons & Co., Inc. It is a sterilized buffered isotonic aqueous solution containing boric acid, sodium borate, sodium chloride (0.7 weight percent) and preserved with thimerosal (0.001 weight percent) and edetate disodium. In the working Examples the lenses are equilibrated or leached for about 48 hours.

Atelocollagen (telopeptide-poor collagen) used in the Examples is prepared from split calf hide (obtained from Ocean Leather Co.) by grinding the hide into fibers, washing with sodium bicarbonate solution and water respectively, centrifuging to remove liquids, and dissolving in water of pH 3. The collagen solution is then treated with pepsin for 5–10 days. Pepsin is known to digest the protease labile nonhelical end regions of the tropocollagen. These structures are termed "telepeptides" and when digested with proteolytic enzymes, the collagen is considered "telopeptide-poor". Stenzel et al have coined the term "atelocollagen" to describe such solubilized collagen (K. Stenzel et al, "Collagen as a Biomaterial," Annual Review of Biophysics and Bio-Engineering 3: 231–53 (1974)). The resulting atelocollagen solution is then filtered through 0.65 Millipore filter and reprecipitated at elevated pH. The fibrous collagen is centrifuged to remove liquid and extracted impurities therefrom and is thereafter freeze-dried. The collagen used in Examples 1–2 is acid soluble calf skin collagen obtained from Calbiochem-Behring Corporation.

The plastic lens mold system used in the Examples are described in U.S. Pat. Nos. 4,121,896 and 4,208,364 which patents are hereby incorporated by reference as if their full texts were set out in this specification.

EXAMPLE 1

In one vessel collagen (3.5 grams) is soaked in 39.5 cc of distilled water and hereafter its pH is adjusted with 0.1M HCl to pH 3. The mixture is homogenized thoroughly until a clear gel results. In a second vessel there is dissolved 0.07 gram of N-methylolacrylamide in 6.93 grams of N,N'-dimethylacrylamide. Both solutions are mixed together, transferred into disposable plastic syringes, degassed under vacuum, and centrifuged at 4,000 rpm for 60 minutes at 15° C. to remove air bubbles. The resulting solution comprising N,N-dimethylacrylamide and collagen is injected from the syringe into plastic contact lens molds under a nitrogen atmosphere. The molds are then transferred to nitrogen filled plastic bags and placed in a plastic vessel of ice contained therein. The polymerization is effected by exposure to $Co^{60}$ radiation for a period of 1.5 hours, the total dosage being 1.5 Mrads. After polymerization is complete, the lenses are removed from the molds and equilibrated in Boil 'N Soak ® solution for 72 hours. The lenses are transparent, biologically stable, and mechanically comparable to commercial Hydron ® lenses. Its water content is 82 percent by weight.

EXAMPLE 2

Collagen (3.5 grams) and chondroitin sulfate (0.35 gram), in their fibrous form, are mixed together in a small, high-speed blender. The mixture is then transferred to a 25 cc round-bottom flask and heated to 60° C. under vacuum (0.1–0.5 mm Hg) for a period of four hours to enhance the condensation reaction between the carboxyl groups of collagen and the hydroxyl groups of chondroitin sulfate. The resulting reaction product mixture is transferred to a small beaker and 39.5 cc of distilled water is added thereto. This mixture is agitated until a homogeneous mass is formed It is allowed to swell overnight. Thereafter, the mixture is adjusted to a pH of 3 with 0.1M HCl and then agitated until homogeneous and clear. In a separate beaker there is dissolved 0.14 gram of N,N'-methylenebisacrylamide in 6.86 grams of N,N-dimethylacrylamide. Both solutions are added together and thoroughly mixed, then transferred into disposable plastic syringes, degassed under vacuum (0.5–0.5 mm Hg), and centrifuged at 4,000 rpm for 60 minutes at 15° C. to remove air bubbles. The resulting gel is injected into plastic lens molds and the procedure and conditions of Example 1 followed. There is obtained contact lenses which are optically clear, biologically stable, and mechanically strong. The lenses are further characterized by 80 percent by weight water content.

EXAMPLE 3

Atelocollagen (3.5 grams) is allowed to swell overnight in 43 cc of distilled water, then acidified with 0.1M HCl, and thereafter homogenized into a clear gel. In a separate container, there is dissolved 0.04 gram of N,N-methylenebisacrylamide in 3.47 grams of N,N-dimethylacrylamide. Both solutions are then mixed together. The resulting gel is transferred into plastic disposable syringes, degassed under vacuum, centrifuged at 4,000 rpm at 15° C. to remove air bubbles, and placed under nitrogen atmosphere. The resulting gel is injected into circlar molds made of glass slides provided with silicon rubber spacers. The slides are transferred into nitrogen filled plastic bags, heat-sealed, and placed into a plastic container with ice cubes. Polymerization is effected by exposure to $Co^{60}$ radiation for a period of 3 hours, the total dosage being 1.0 Mrads. After polymerization is complete, the resulting hydrogel discs are leached for 72 hours in Boil 'N Soak solution. There is obtained a hydrogel product which is characterized by excellent light transmission, 86 percent by weight water content, and non-biodegradability. Its mechanical strength is comparable to Hydron ® lenses. The hydrogel product is dried and analyzed by infrared (IR) absorption. Its IR spectrum is compared to IR scans of pure collagen and pure poly(dimethylacrylamide). The IR spectrum of this product shown absorption characteristics for both pure collagen and poly(dimethylacrylamide) plus new absorption bands at 800 $cm^{-1}$ and 1020 $cm^{-1}$ which indicates formation of a graft copolymer.

EXAMPLE 4

Atelocollagen (3.5 grams) is allowed to hydrate overnight in 39.5 cc of 1M glucose (which contains 0.25 gram of sodium thiosulfate and 8 grams of ethylene glycol), is acidified with 0.25M citric acid to pH 3 and then homogenized to a clear gel. Thereafter, its pH is raised to 7 with 2M sodium hydroxide. Precipitation of the atelocollagen does not occur due to the presence of the glucose. In a separate vessel, 0.07 gram of N,N'-methylenebisacrylamide is dissolved in 6.93 grams of N,N-dimethylacrylamide. The atelocollagen gel and amide solution are mixed together, homogenized, and maintained at about −5° C. A solution of crosslinking agents and initiator is prepared by dissolving 0.125 gram of 1-ethyl-3-(3-dimethylamino-n-propyl)carbodiimide hydrochloride, 0.079 gram of N-hydroxysuccinamide, and 0.25 gram of potassium persulfate. The solution of crosslinking agents and the atelocollagen/amide solution are added together, under agitation, and maintained below 0° C. The resulting solution is transferred into cold plastic disposable syringes and centrifuged for 20 minutes at 0° C. and 15,000 rpm to remove air bubbles, and thereafter is injected into molds of desired shape and allowed to react overnight at room temperature, e.g., about 20° C. or slightly above room temperature. The resulting products are then leached for 48 hours in Boil 'N Soak Solution. There are obtained membranes which are transparent, flexible and non-biodegradable. The water content of these membranes is about 80 percent by weight.

The products obtained from Examples 1 through 3 are compared with commercial Hydron polymer and irradiated cross-linked collagen with respect to water content, tear strength, biodegradability, and oxygen permeability. The data is set forth in Table I below:

TABLE I

| COMPOSITION | Wt. % $H_2O$ | TEAR STRENGTH g $mm^{-1}$ | BIO-DEGRADABILITY(3) | $O_2$ PERMEABILITY × $10^{-10}$(4) |
|---|---|---|---|---|
| HYDRON(1) POLYMER | 38 | 2.2 | nonbio-degradable | 10 |
| COLLAGEN(2) | 91 | 2.5 | liquified after 2 days | 54 |
| EXAMPLE 1 | 82 | 2.6 | nonbio-degradable | 40 |
| EXAMPLE 2 | 80 | 2.5 | nonbio-degradable | 40 |
| EXAMPLE 3 | 86 | 2.2 | nonbio-degradable | 43 |

(1)Prepared from a mixture containing about 99 wt. % hydroxyethyl methacrylate, about 0.3–0.5 wt. % ethylene glycol dimethacrylate, and diisopropyl peroxydicarbonate as the catalyst therefor
(2)Gamma-irradiated crosslinked collagen gel.
(3)Visual observation after 12 days.
(4)Values from $O_2$ permeability - % water relationship.

From a consideration of the data presented in TABLE I supra the following observations can be made. Gamma-irradiated crosslinked collagen gel is extremely biodegradable and degrades to a liquid solution after two days. On the other hand, the chemically modified collagen/N,N-dimethylacrylamide products of Example 2 and the atelocollagen/N,N-dimethylacrylamide products of Examples 3 and 4 give hydrogel products which have high oxygen permeability, good tear strength, and high water content. Moreover, these products are nonbiodegradable. The characteristics of a typical commercial Hydron polymer (known as "polymacon" in the soft contact lens field) are set forth for purposes of comparison. The novel shaped products are exceptional candidates for use as extended wear soft contact lenses. Their properties of high oxygen permeability and high water uptake are attained without sacrifice in tear strength (actually improved compared to polymacon) and non-biodegradability (far superior to collagen).

EXAMPLE 5

| Composition: | Wt. % | Wt. grams |
|---|---|---|
| Atelocollagen | 5.00 | 1.500 |
| N-isopropylacrylamide | 9.94 | 2.982 |
| N,N'-methylenebisacrylamide | 0.06 | 0.018 |
| Distilled Water | 85.00 | 25.500 |
| | 100.00% | 30.00 g |

Procedure:

a. Dissolve 2.982 g of N-isopropylacrylamide and 0.018 g of N,N'-methylenebisacrylamide in 25.5 g of distilled water.
b. Add 1.5 g of atelocollagen to (a) and disperse thoroughly.
c. Solubilize the atelocollagen in the resulting admixture by acidifying with 1.0M HCl to pH 3.
d. The resulting (lens) solution is filtered through a 10μ filter and filled in a 10 ml disposable plastic syringe. The syringe is placed under vacuum, degassed in few stages, the air being replaced with nitrogen.
e. The syringe containing the degassed lens solution is placed in a centrifuge and centrifuged for one hour at 6000 rpm at 10° C.
f. In the next step, the syringe is transferred into a glove box filled with nitrogen. An amount of the lens solution is injected from the syringe into several bottom mold portions (female mold portions) of the plastic lens mold system. The mold systems are closed by inserting a top mold portion (male mold portion) into each bottom mold portion.

g. The closed molds are placed in plastic bags filled with nitrogen and the bags are sealed. The bags are then transferred into an insulated box and covered with ice.

h. The simultaneous reactions, e.g., polymerization involving the amide monomers, collagen-amide polymer graft reaction, and crosslinking reaction of collagen, is promoted by gamma radiation of 1.0 Mrad total dose. The irradiation is effected by using $Co^{60}$ as the source of radiation, generally, at low temperature, 5°-10° C., in nitrogen atmosphere to minimize any denaturation of collagen and minimize bond scission which can occur during a high energy radiation.

| Properties of the Equilibrated Lenses: | |
|---|---|
| Water Content | 86 wt. % |
| Light Transmission at 660 nm | 97% |
| Tear Strength (Propagation) | 3.0 g/mm |
| Biological Stability | No biodegradability observed. |

EXAMPLE 6

| Composition: | Wt. % | Wt. grams |
|---|---|---|
| Atelocollagen | 5.00 | 1.500 |
| Diacetoneacrylamide | 4.97 | 1.491 |
| N,N-dimethylacrylamide | 4.97 | 1.491 |
| N,N'-methylenebisacrylamide | 0.06 | 0.018 |
| Distilled Water | 85.00 | 25.500 |
| | 100.00% | 30.00 g |

Procedure:

a. Diacetoneacrylamide (1.491 g) and 0.018 g of N,N'-methylenebisacrylamide are dissolved in a solution of 25.5 g of distilled water containing 1.491 g of N,N-dimethylacrylamide.

b. To the aqueous monomeric solution of step (a) there is added and dispersed therein 1.5 g of atelocollagen.

c. Atelocollagen in the resulting admixture is solubilized by adding 1.0M HCl until pH 3 is reached.

d. Continue with step (d) of *and the subsequent steps* of Example 5.

| Properties of the Equilibrated Lenses: | |
|---|---|
| Water Content | 86.5 wt. % |
| Light Transmission at 660 nm | 97% |
| Tear Strength (Propagation) | 2.2 g/mm |
| Biological Stability | No biodegradability observed. |

EXAMPLE 7

| Composition: | Wt. % | Wt. grams |
|---|---|---|
| Atelocollagen | 5.00 | 1.250 |
| N-isopropylacrylamide | 4.97 | 1.243 |
| N,N-dimethylacrylamide | 4.97 | 1.243 |
| N,N'-methylenebisacrylamide | 0.06 | 0.15 |
| Distilled Water | 85.00 | 21.250 |
| | 100.00% | 25.00 g |

Procedure:

a. Atelocollagen (1.25 g) is dispersed in 21.25 g of distilled water.

b. Atelocollagen is solubilized in step (a) by adding 1.0M HCl until pH 3 is reached.

c. N-isopropylacrylamide (1.243) and 0.015 g of N,N'-methylenebisacrylamide are dissolved in 1.243 g of N,N-dimethylacrylamide. This monomeric amide solution is added to the atelocollagen solution (step b) and the resulting solution agitated until homogeneous.

d. Continue with step (d) *and the subsequent steps* of Example 5.

| Properties of the Equilibrated Lenses: | |
|---|---|
| Water Content | 88 wt. % |
| Light Transmission at 660 nm | 99% |
| Tear Strength (Propagation) | 2.0 g/mm |
| Biological Stability | No biodegradability observed. |

EXAMPLE 8

| Composition: | Wt. % | Wt. grams |
|---|---|---|
| Atelocollagen | 5.00 | 1.250 |
| N,N-dimethylacrylamide | 4.95 | 1.238 |
| Hydroxyethyl Methacrylate | 4.95 | 1.238 |
| N,N'-methylenebisacrylamide | 0.10 | 0.025 |
| Distilled Water | 85.00 | 21.250 |
| | 100.00% | 25.00 g |

Procedure:

a. Atelocollagen (1.25 g) is dispersed in 21.25 g of distilled water and solubilized by adjusting the pH with 1.0M HCl to pH 3.

b. N,N'-methylenebisacrylamide (0.025 g) is dissolved in a solution of 1.238 g of N,N-dimethylacrylamide and 1.238 g of 2-hydroxyethyl methacrylate.

c. The solution of step (b) is added to the atelocollagen solution of step (a) and agitated until homogeneous.

d. Continue with step (d) *and the subsequent steps* of Example 5.

| Properties of the Equilibrated Lenses: | |
|---|---|
| Water Content | 89 wt. % |
| Light Transmission at 660 nm | 97% |
| Tear Strength (Propagation) | 0.8 g/mm |
| Biological Stability | No biodegradability observed. |

EXAMPLE 9

| Composition: | Wt. % | Wt. grams |
|---|---|---|
| Atelocollagen | 9.0 | 2.7 |
| Distilled Water | 91.0 | 27.3 |
| | 100.00% | 30.0 g |

Procedure:

a. Atelocollagen (2.7 g) is dispersed in 27.3 g of distilled water and solubilized by bringing the pH to pH 3 with 1.0M HCl.

b. Continue with step (d) *and the subsequent steps* of Example 5.

| Properties of the Equilibrated Lenses: | |
|---|---|
| Water Content | 91 wt. % |

-continued

| Properties of the Equilibrated Lenses: | |
|---|---|
| Light Transmission at 660 nm | 96% |
| Tear Strength (Propagation) | 3.8 g/mm |
| Biological Stability | Total liquefaction in 24 hours. |

EXAMPLE 10

| Composition: | Wt. % |
|---|---|
| Atelocollagen | 7.0 |
| N-isopropylacrylamide | 7.0 |
| N,N'-methylenebisacrylamide | 0.1 |
| Distilled Water | 85.9 |
| | 100.00% |

Procedure:

a. Dissolve the N-isopropylacrylamide and N,N'-methylenebisacrylamide in distilled water.
b. Add the atelocollagen to (a) and disperse thoroughly.
c. Solubilize the atelocollagen in the resulting admixture by acidifying with 1.0M HCl to pH 3.
d. Continue with step (d) *and the subsequent steps* of Example 5.

| Properties of the Equilibrated Lenses: | |
|---|---|
| Water Content | 86.3 wt. % |
| Light Transmission at 660 nm | 91.4% |
| Biological Stability | No biodegradability observed. |

EXAMPLE 11

| Composition: | Wt. % |
|---|---|
| Atelocollagen | 7.0 |
| Poly(N,N-dimethylacrylamide) | 7.0 |
| Distilled Water | 86.00 |
| | 100.00% |

The poly(N,N-dimethylacrylamide) employed in this Example is obtained via the polymerization of an aqueous solution of 50 weight percent N,N-dimethylacrylamide. Polymerization is initiated using 0.5 wt. % $(NH_4)_2S_2O_8$ plus 0.5 wt. % $NaHSO_3$ redox system at 20° C. An exothermic temperature of about 60° C. is reached. The resulting poly(N,N-dimethylacrylamide) product is precipitated from acetone and vacuum dried at 80° C. Its molecular weight is of the order of 500,000

Procedure:

a. To an aqueous [monomeric] solution of the poly(N,N-dimethylacrylamide) there is added and dispersed therein the atelocollagen.
b. Atelocollagen in the resulting admixture is solubilized by adding 1.0M HCl until pH 3 is reached.
c. Continue with step (d) *and the subsequent steps* of Example 5.

| Properties of the Equilibrated Lenses: | |
|---|---|
| Water Content | 90.1 wt. % |
| Light Transmission at 660 nm | 87.6% |
| Biological Stability | Liquefied after 24 hours. |

FIG. 2 is the infrared spectrum of the atelocollagen/-poly(N,N-dimethylacrylamide) "product" of Example 11. Its IR spectrum and the IR spectrum of atelocollagen are very similar.

Figure 1:
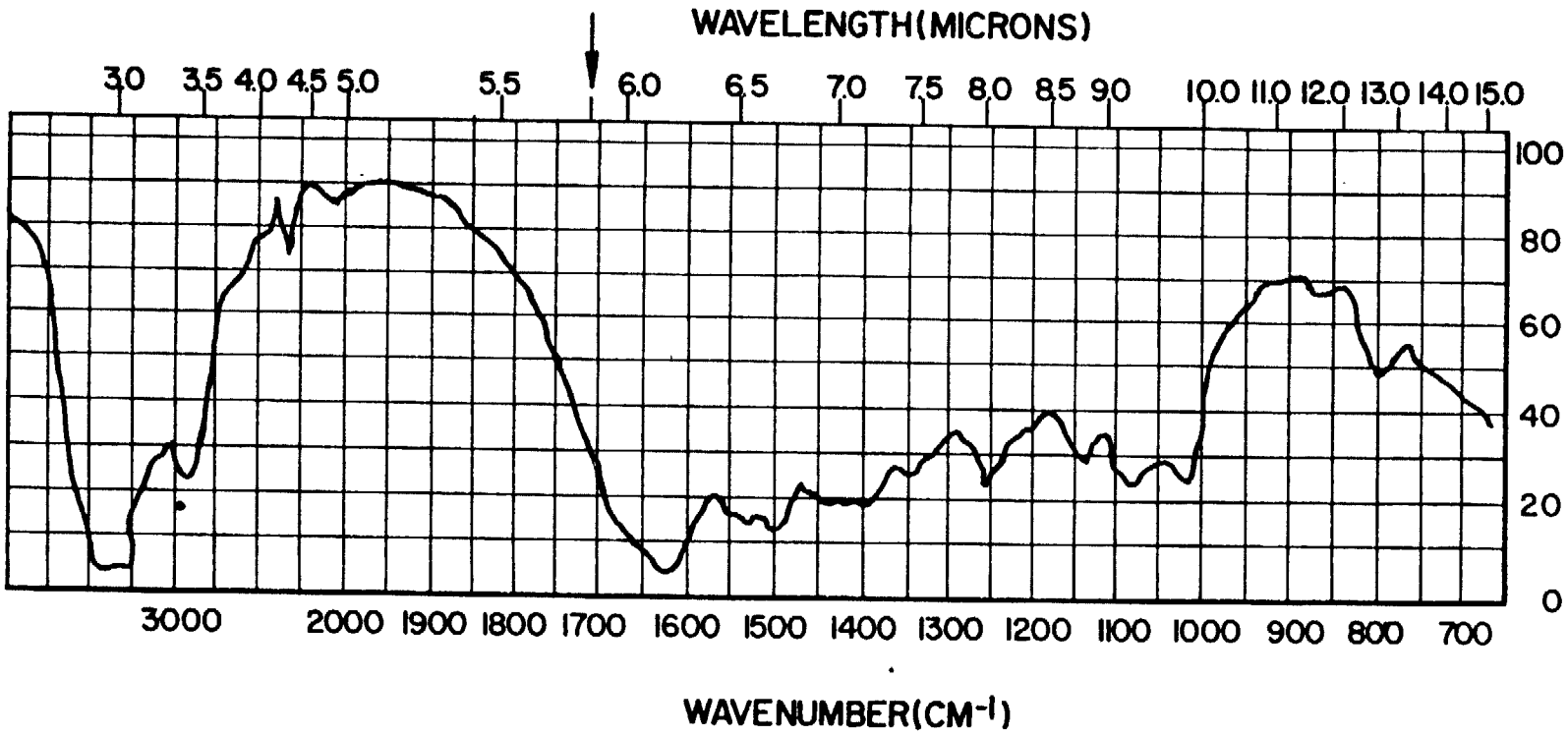
FIG. 1 is the infrared (IR) spectrum of the cross-linked atelocollagen/N,N-dimethylacrylamide product of Example 10. Its IR spectrum exhibits a sharp peak at 1260 $cm^{-1}$ and new absorption peaks at 800 $cm^{-1}$ and 1020 $cm^{-1}$, not found in collagen or N,N-dimethylacrylamide, indicating formation of new bonds attributable apparently to collagen-N,N-dimethylacrylamide grafts.
Figure 2:
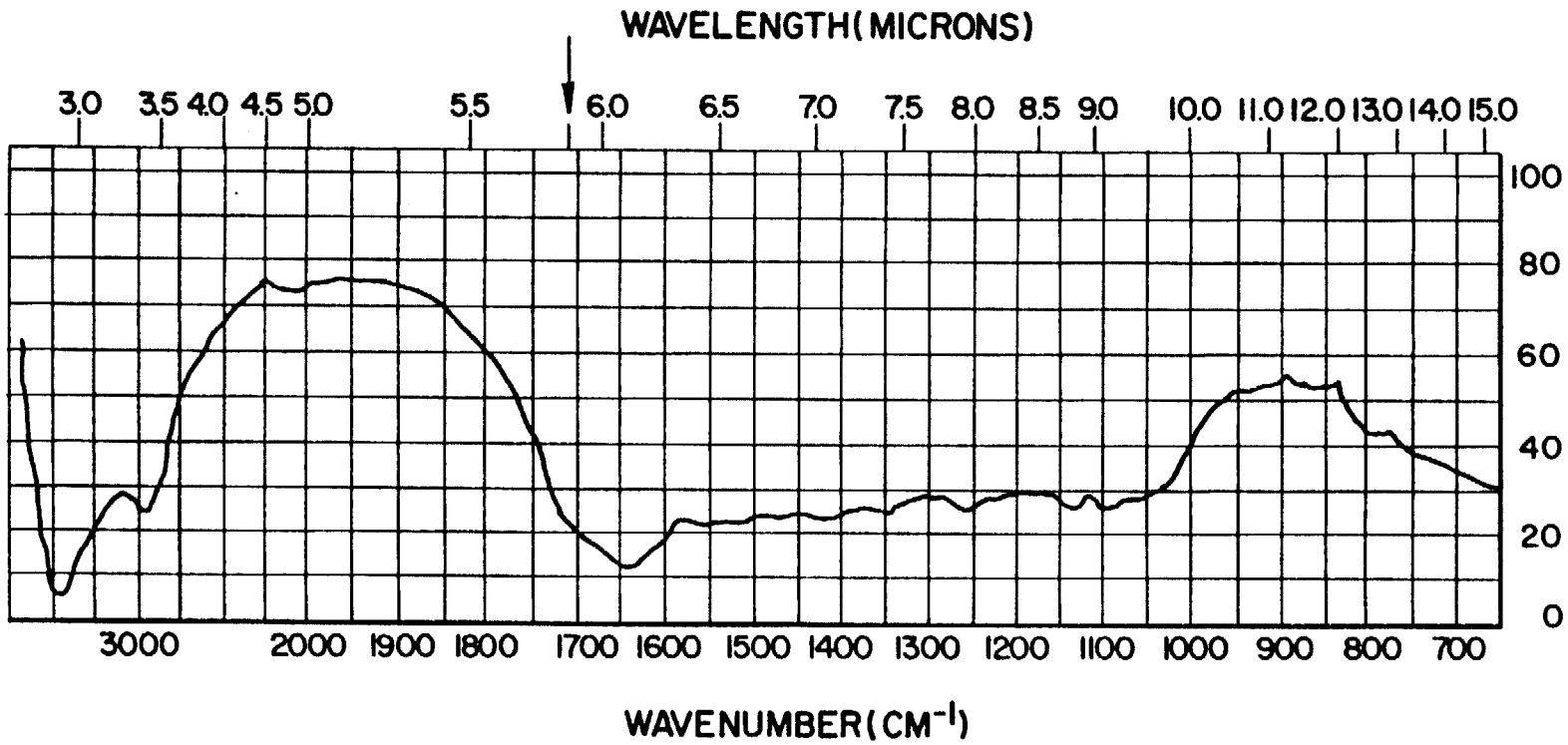
Figure 3:
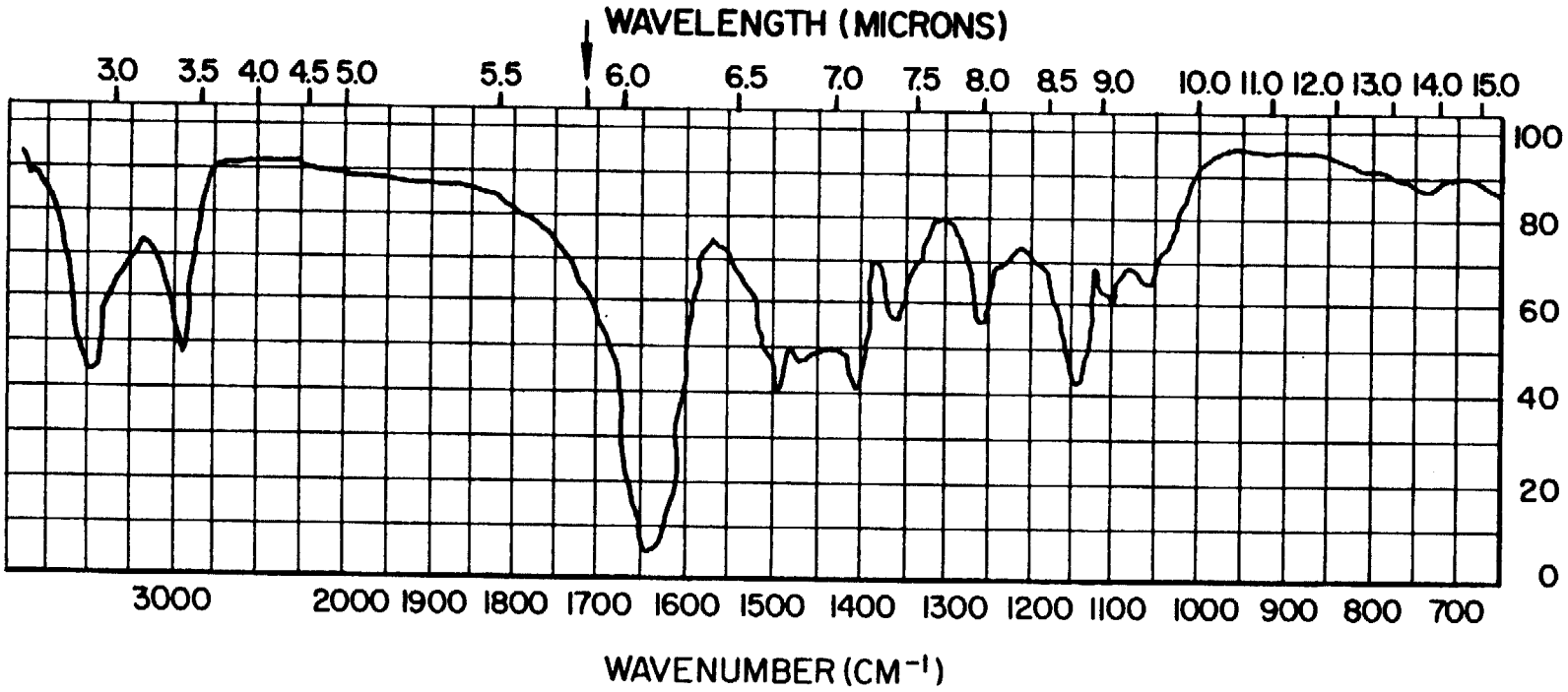
FIG. 3 is the infrared spectrum of the poly(N,N-dimethylacrylamide) and is included in this discussion for purposes of comparison with the IR spectra of FIGS. 1 and 2.
Figure 4:
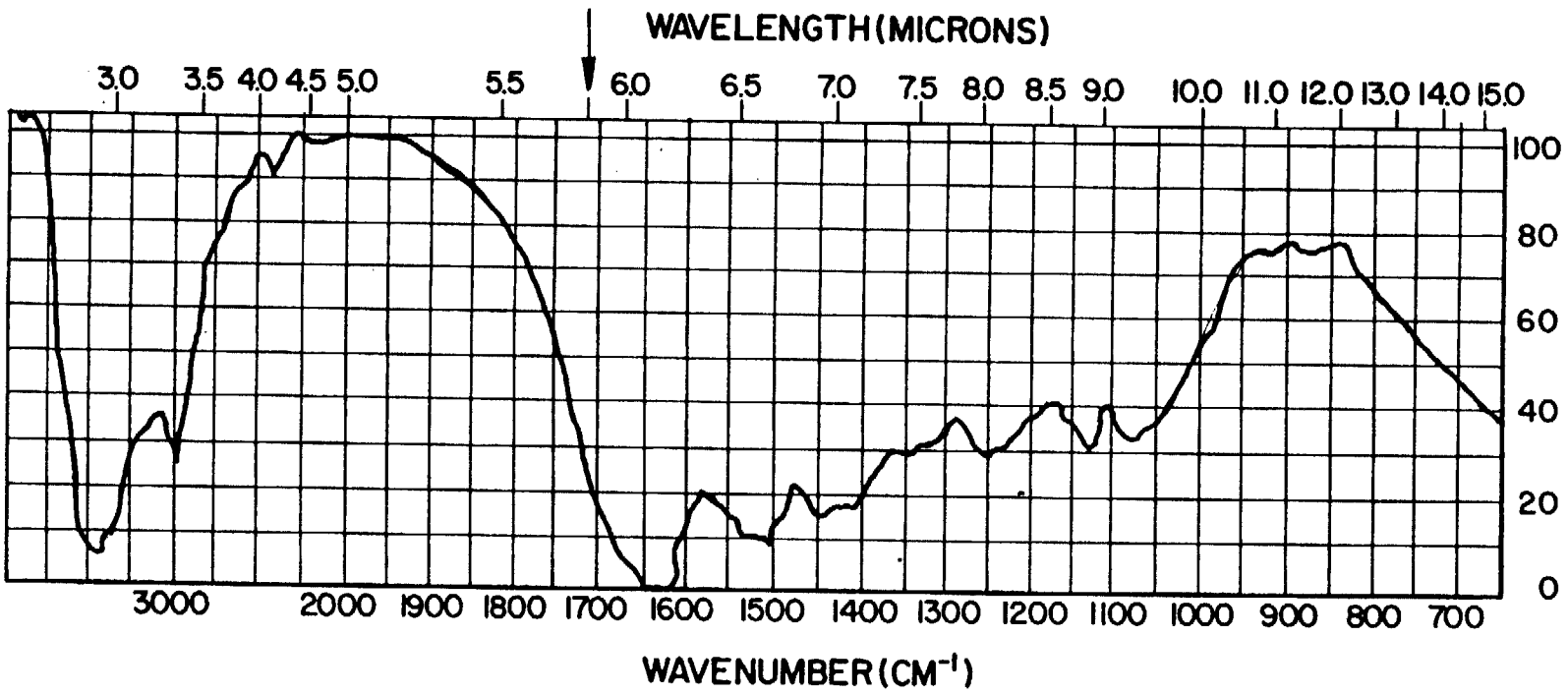

FIG. 4 is the infrared spectrum of atelocollagen after gamma-irradiation (Example 9 above). The IR spectrum of gamma-irradiated atelocollagen (Example 9, FIG. 4) and the IR spectrum of atelocollagen/-poly(N,N-dimethylacrylamide) "product" (Example 11; FIG. 2) are very similar. The IR spectrum of the "product" of Example 11 confirms that the poly(dimethylacrylamide) component was extracted during the equilibration or leaching step.

What is claimed is:

1. A polymerized hydrophilic water-swellable composition made from a mixture of components consisting essentially of:
   (a) solubilized collagen; and
   (b) an ethylenically unsaturated monomer of the group consisting of the following:
      (i) the unsubstituted, N-substituted and N,N-disubstituted 2-alkenamides wherein each N substituent is hydrogen or a $(C_1-C_6)$alkyl, and wherein the 2-alkenoyl group of the 2-alkenamide molecule contains from 2-6 carbon atoms;
      (ii) the vicinal-epoxyalkyl 2-alkenoates wherein the vicinal-epoxyalkyl group contains from 2 to 4 carbon atoms and wherein the 2-alkenoate group contains from 2-6 carbon atoms;
      (iii) the hydroxy(alkoxy)$_n$alkyl 2-alkenoates wherein the alkyl and alkoxy groups contain from 2 to 4 carbon atoms, and wherein n is an integer of from zero to 4, and wherein the 2-alkenoate group contains from 2 to 6 carbon atoms;
      (iv) the alkoxy(alkoxy)$_n$alkyl 2-alkenoates wherein the alkyl and alkoxy groups contain from 2 to 4 carbon atoms, with the proviso that the terminal alkoxy group contains from 1 to 4 carbon atoms, wherein n is an integer of from zero to 4, and wherein the 2-alkenoate group contains from 2 to 6 carbon atoms;
      (v) the dialkylaminoalkyl 2-alkenoates wherein the alkyl groups contain from 1 to 4 carbon atoms and wherein the 2-alkenoate group contains from 2 to 6 carbon atoms; and
      (vi) N-vinylpyrrolidone;
   (c) said polymerized hydrophilic composition containing from 0.5 to less than 50 weight percent of solubilized collagen [and] from 99.5 to about 50 weight percent of ethylenically unsaturated monomer units, based on the total weight of the components *and bonds attributable to grafts.*

2. A shape-retaining hydrogel of the composition of claim 1 having a water content upwards to 95 weight percent.

3. A shape-retaining hydrogel of claim 2 wherein the components expressed as weight percent, based on the total weight of said components, are as follows:

| COMPONENT | WEIGHT PERCENT |
|---|---|
| Ethylenically Unsaturated Monomer | ~50–99.5 |
| Solubilized Collagen | <50–0.5 |
| Modifier | 0–35 |
| Crosslinking Agent | 0–5 |

and wherein said hydrogel has a water content of from about 55 to about 95 weight percent.

4. A shape-retaining hydrogel of claim 2 wherein the components expressed as weight percent, based on the total weight of said components, are as follows:

| COMPONENT | WEIGHT PERCENT |
|---|---|
| Ethylenically Unsaturated Monomer | ~60–95 |
| Solubilized Collagen | ~5–45 |
| Modifier | 0–30 |
| Crosslinking Agent | 0–2 |

and wherein said hydrogel has a water content of from about 65 to about 90 weight percent.

5. A shape-retaining hydrogel of claim 2 wherein the components expressed as weight percent, based on the total weight of said components, are as follows:

| COMPONENT | WEIGHT PERCENT |
|---|---|
| Ethylenically Unsaturated Monomer | ~68–90 |
| Solubilized Collagen | ~10–35 |
| Modifier | 0–20 |
| Crosslinking Agent | 0–1 |

and wherein said hydrogel has a water content of from about 65 to about 90 weight percent.

6. The hydrogel of claim 2 which is characterized by biocompatibility with living tissue, substantial non-biodegradability, high oxygen permeability, and high water content.

7. The hydrogel of claim 3 in the form of a contact lens, said hydrogel characterized by biocompatibility with living tissue, substantial non-biodegradability, high oxygen permeability, and high water content.

8. The hydrogel of claim 4 in the form of a contact lens, said hydrogel characterized by biocompatibility with living tissue, substantial non-biodegradability, high oxygen permeability, and high water content.

9. The hydrogel of claim 5 in the form of a contact lens, said hydrogel characterized by biocompatibility with living tissue, substantial non-biodegradability, high oxygen permeability, and high water content.

10. The shape-retaining hydrogel of claim 8 wherein said ethylenically unsaturated monomers are the unsubstituted, N-substituted and N,N-disubstituted 2-alkenamides wherein each N substituent is hydrogen or a $(C_1-C_6)$alkyl, and wherein the 2-alkenoyl group of the 2-alkenamide molecule contains from 2–6 carbon atoms.

11. The shape-retaining hydrogel of claim 8 wherein said ethylenically unsaturated monomers are the vicinal-epoxyalkyl 2-alkenoates wherein the vicinal-epoxyalkyl group contains from 2 to 4 carbon atoms and wherein the 2-alkenoate group contains from 2–6 carbon atoms.

12. The shape-retaining hydrogel of claim 8 wherein said ethylenically unsaturated monomers are the hydroxy(alkoxy)$_n$alkyl 2-alkenoates wherein the alkyl and alkoxy groups contain from 2 to 4 carbon atoms, wherein n is an integer of from zero to 4, and wherein the 2-alkenoate group contains from 2 to 6 carbon atoms.

13. The shape-retaining hydrogel of claim 8 wherein said ethylenically unsaturated monomers are the alkoxy(alkoxy)$_n$alkyl 2-alkenoates wherein the alkyl and alkoxy groups contain from 2 to 4 carbon atoms, with the proviso that the terminal alkoxy group contains from 1 to 4 carbon atoms, wherein n is an integer of from zero to 4, and wherein the 2-alkenoate group contains from 2 to 6 carbon atoms.

14. The shape-retaining hydrogel of claim 8 wherein said ethylenically unsaturated monomers are the dialkylaminoalkyl 2-alkenoates wherein the alkyl groups contain from 1 to 4 carbon atoms and wherein the 2-alkenoate group contains from 2 to 6 carbon atoms.

15. The shape-retaining hydrogel of claim 8 wherein said ethylenically unsaturated monomer is N-vinylpyrrolidone.

16. The shape-retaining hydrogel of claim 7 wherein said ethylenically unsaturated monomer is N,N-dimethylacrylamide.

17. The shape-retaining hydrogel of claim 8 wherein said ethylenically unsaturated monomer is N,N-dimethylacrylamide.

18. The shape-retaining hydrogel of claim 9 wherein said ethylenically unsaturated monomer is N,N-dimethylacrylamide.

19. A process for preparing shape-retaining hydrogels which comprises preparing an aqueous solution of reactants comprising (a) solubilized collagen; and (b) an ethylenically unsaturated monomer defined in claim 1;

(c) said solution containing less than 30 weight percent of said collagen and at least about 50 to about 99.5 weight percent of said ethylenically unsaturated monomer based on the total weight of the reactants;

(d) effecting the polymerization reaction of said aqueous solution of reactants in a mold using cross-linking means of the group consisting of irradiation, polyethylenically unsaturated cross-linking compounds, and mixtures thereof;

(e) for a period of time sufficient to produce shape-retaining hydrogel products *which contain bonds attributable to grafts*; and (f) recovering said hydrogel product.

20. The process of claim 19 wherein said aqueous solution of reactants comprises a polyethylenically unsaturated crosslinking compound, and from about 0.5 to about 12 weight percent of said solubilized collagen.

21. The process of claim 20 wherein said crosslinking means comprises irradiation.

[22. The process of claim 21 wherein said aqueous solution of reactants comprises an ethylenically unsaturated monomer defined in claim 1.]

23. The process of claim 22 wherein said aqueous solution of reactants comprises [an ethylenically unsaturated monomer defined in claim 10] *unsubstituted, N-substituted and N,N-disubstituted 2-alkenamides wherein each N substituent is hydrogen or a $(C_1-C_6)$alkyl, and wherein the 2-alkenoyl group of the 2-alkenamide molecule contains from 2–6 carbon atoms.*

24. The process of claim 22 wherein said aqueous solution of reactants comprises [an ethylenically unsaturated monomer defined in claim 11] *the vicinal-epoxyalkyl 2-alkenoates wherein the vicinal-epoxyalkyl group contains from 2 to 4 carbon atoms and wherein the 2-alkenoate group contains from 2–6 carbon atoms.*

25. The process of claim 22 wherein said aqueous solution of reactants comprises [an ethylenically unsaturated monomer defined in claim 12] *the hydroxy(alkoxy)alkyl 2-alkenoates wherein the alkyl and alkoxy groups contain from 2 to 4 carbon atoms, wherein n is an integer of from zero to 4, and wherein the 2-alkenoate group contains from 2 to 6 carbon atoms.*

26. The process of claim 22 wherein said aqueous solution of reactants comprises [an ethylenically unsaturated monomer defined in claim 13] *the alkoxy(alkoxy)$_n$alkyl 2-alkenoates wherein the alkyl and alkoxy groups contain from 2 to 4 carbon atoms, with the proviso that the terminal alkoxy group contains from 1 to 4 carbon atoms, wherein n is an integer of from zero to 4, and wherein the 2-alkenoate group contains from 2 to 6 carbon atoms.*

27. The process of claim 22 wherein said aqueous solution of reactants comprises [an ethylenically unsaturated monomer defined in claim 14] *the dialkylaminoalkyl 2-alkenoates wherein the alkyl groups contain from 1 to 4 carbon atoms and wherein the 2-alkenoate group contains from 2 to 6 carbon atoms.*

28. The process of claim 22 wherein said aqueous solution of reactants comprises [an ethylenically unsaturated monomer defined in claim 15] *N-vinylpyrrolidone.*

29. The process of claim 22 wherein said aqueous solution of reactants comprises [an ethylenically unsaturated monomer defined in claim 16] *N,N-dimethacrylamide.*

* * * * *